US008173432B2

(12) United States Patent
Balas (10) Patent No.: US 8,173,432 B2
(45) Date of Patent: May 8, 2012

(54) METHOD AND SYSTEM FOR CHARACTERIZATION AND MAPPING OF TISSUE LESIONS

(75) Inventor: Constantinos Balas, Crete (GR)

(73) Assignee: Forth Photonics Ltd., London (GB)

(*) Notice: Subject to any disclaimer, the term of this patent is extended or adjusted under 35 U.S.C. 154(b) by 834 days.

(21) Appl. No.: 10/978,101

(22) Filed: Oct. 29, 2004

(65) Prior Publication Data

US 2005/0090751 A1  Apr. 28, 2005

Related U.S. Application Data

(63) Continuation of application No. 10/346,338, filed on Jan. 16, 2003, now abandoned, which is a continuation of application No. 09/739,089, filed on Dec. 15, 2000, now abandoned.

(30) Foreign Application Priority Data

Mar. 28, 2000 (GR) .............................. 20000100102

(51) Int. Cl.
*G01N 21/84* (2006.01)
(52) U.S. Cl. ............. 436/63; 436/64; 436/164; 436/172
(58) Field of Classification Search .................. 436/63, 436/64, 164, 172
See application file for complete search history.

(56) References Cited

U.S. PATENT DOCUMENTS

| 4,071,020 A | 1/1978 | Pugliese |
| 4,273,110 A | 6/1981 | Groux et al. |
| 5,235,984 A | 8/1993 | D'Sa |
| 5,421,339 A | 6/1995 | Ramanujam et al. |
| 5,424,543 A | 6/1995 | Dombrowski et al. |

(Continued)

FOREIGN PATENT DOCUMENTS

WO   WO-92/19148 A1   12/1992

(Continued)

OTHER PUBLICATIONS

Andersson-Engels, Stefan et al., "Preliminary Evaluation of Two Fluorescence Imaging Methods for the Detection and the Delineation of Basal Cell Carcinomas of the Skin," *Lasers in Surgery and Medicine*, vol. 26:76-82 (2000).

(Continued)

*Primary Examiner* — Jill Warden
(74) *Attorney, Agent, or Firm* — Nixon & Vanderhye P.C.

(57) ABSTRACT

The present invention provides a method and an apparatus for the in vivo, non-invasive, early detection of alterations and mapping of the grade of these alterations, caused in the biochemical and/or in the functional characteristics of epithelial tissues during the development of tissue atypias, dysplasias, neoplasias and cancers. The method is based, at least in part, on the simultaneous measurement of the spatial, temporal and spectral alterations in the characteristics of the light that is re-emitted from the tissue under examination, as a result of a combined tissue excitation with light and special chemical agents. The topical or systematic administration of these agents result in an evanescent contrast enhancement between normal and abnormal areas of tissue. The apparatus enables the capturing of temporally successive imaging in one or more spectral bands simultaneously. Based on the measured data, the characteristic curves that express the agent-tissue interaction kinetics, as well as numerical parameters derived from these data, are determined in any spatial point of the examined area. Mapping and characterization of the lesion, are based on these parameters.

4 Claims, 7 Drawing Sheets

U.S. PATENT DOCUMENTS

| | | |
|---|---|---|
| 5,450,857 A | 9/1995 | Garfield et al. |
| 5,647,368 A | 7/1997 | Zeng et al. |
| 5,697,373 A | 12/1997 | Richards-Kortum et al. |
| 5,771,317 A | 6/1998 | Edgar |
| 5,791,346 A | 8/1998 | Craine et al. |
| 5,842,995 A | 12/1998 | Mahadevan-Jansen et al. |
| 5,920,399 A | 7/1999 | Sandison et al. |
| 5,921,926 A | 7/1999 | Rolland et al. |
| 5,956,144 A | 9/1999 | Kaplan et al. |
| 5,989,184 A | 11/1999 | Blair |
| 6,101,408 A | 8/2000 | Craine et al. |
| 6,134,010 A | 10/2000 | Zavislan |
| 6,159,445 A | 12/2000 | Klaveness et al. |
| 6,187,289 B1 | 2/2001 | Richards-Kortum et al. |
| 6,292,683 B1 | 9/2001 | Gupta et al. |
| 6,299,858 B1 | 10/2001 | Serbedzija et al. |
| 6,299,860 B1 | 10/2001 | Luiken |
| 6,332,092 B1 | 12/2001 | Deckert et al. |
| 6,370,422 B1 | 4/2002 | Richards-Kortum et al. |
| 6,411,835 B1 | 6/2002 | Modell et al. |
| 6,902,935 B2 * | 6/2005 | Kaufman et al. ............... 436/63 |
| 2002/0007122 A1 | 1/2002 | Kaufman et al. |
| 2002/0127735 A1 | 9/2002 | Kaufman et al. |
| 2002/0197728 A1 * | 12/2002 | Kaufman et al. ............ 436/164 |
| 2004/0111031 A1 | 6/2004 | Alfano et al. |

FOREIGN PATENT DOCUMENTS

| | | |
|---|---|---|
| WO | WO-98/24369 A1 | 6/1998 |
| WO | WO-99/18847 A1 | 4/1999 |
| WO | WO-01/72214 A1 | 10/2001 |

OTHER PUBLICATIONS

Balas, Costas et al., "In-vivo assessment of acetic acid-cervical tissue interaction using quantitative imaging of backscattered light: its potential use for in-vivo cervical cancer detection grading and mapping," *Part of teh EUROPTO Conference on Optical Biopsy*, Stockholm, Sweden, vol. 3568:31-37 (1998).

Balas, Costas J. et al., "In vivo detection and staging of epithelial dysplasias and malignancies based on the quantitative assessment of acetic acid-tissue interaction kinetics," *J. Photochem. Photobiol. B: Biol.*, vol. 53:153-157 (1999).

Glanzmann, Thomas et al., "Time-resolved spectrofluorometer for clinical tissue characterization during endoscopy," *Review of Scientific Instruments*, vol. 70(10):4067-4077 (1999).

Stefanaki, Irene M. et al., "In vivo detection of human papilloma virus-induced lesions of anogenital area after application of acetic acid: a novel and accurate approach to a trivial method," *Journal of Photochemistry and Photobiology B: Biology*, vol. 65:115-121 (2001).

Examination Report dated May 14, 2010 in Brazilian Appln. No. PI 0108944-7 with English Translation.

* cited by examiner

Figure 7

METHOD AND SYSTEM FOR CHARACTERIZATION AND MAPPING OF TISSUE LESIONS

RELATED APPLICATIONS

This application is a continuation application of U.S. application Ser. No. 10/346,338, filed on Jan. 16, 2003, now abandoned, which is a continuation of U.S. application Ser. No. 09/739,089, filed on Dec. 15, 2000, now abandoned, which in turn claims priority to Greek National Application Serial No. 20000100102 filed on Mar. 28, 2000. The contents of all of the aforementioned application(s) are hereby incorporated by reference.

FIELD OF THE INVENTION

The present invention is directed to a method and apparatus for the in vivo, non invasive detection and mapping of the biochemical and/or functional pathologic alterations of human tissues.

BACKGROUND OF THE INVENTION

Cancer precursors signs are the so called pre-cancerous states, which are curable if they are detected at an early stage. In the opposite case the lesion can progress in depth, resulting in the development of invasive cancer and metastases. At this stage, the possibilities of successful therapy are dramatically diminished. Consequently, the early detection and the objective identification of the severity (stage) of the precancerous lesion are of crucial importance.

The conventional clinical process of optical examination have very limited capabilities in detecting cancerous and pre-cancerous tissue lesions. This is due to the fact that the structural and metabolic changes, which take place during the development of the disease, do not significantly and with specificity alter the color characteristics of the pathological tissue.

In order to obtain more accurate diagnosis, biopsy samples are obtained from suspicious areas, which are submitted for histological examination. However, biopsy sampling poses several problems, such as: a) risk for sampling errors associated with the visual limitations in detecting and localizing suspicious areas; b) biopsy can alter the natural history of the intraepithelial lesion; c) mapping and monitoring of the lesion require multiple tissue sampling, which is subjected to several risks and limitations; d) the diagnostic procedure performed with biopsy sampling and histologic evaluation is qualitative, subjective, time consuming, costly and labor intensive. In recent years there have been developed and presented quite a few new methods and systems in an effort to overcome the disadvantages of the conventional diagnostic procedures. These methods can be classified in two categories: a) Methods which are based on the spectral analysis of tissues in vivo, in an attempt to improve the diagnostic information b) Methods which are based on the chemical excitation of tissues with the aid of special agents, which have the property to interact with pathologic tissue and to alter its optical characteristics selectively, thus enhancing the contrast between lesion and healthy tissue.

In the first case, the experimental use of spectroscopic techniques as a potential solutions to existing diagnostic problems, is motivated by their capability to detect alterations in the biochemical and/or the structural characteristics, which take place in the tissue during the development of the disease. In particular, fluorescence spectroscopy has been extensively used in various tissues, where the later are optically excited with the aid of a light source (usually laser), of short wave length (blue-ultraviolet range) and their response is measured as fluorescence intensity vs. wavelength.

Garfield and Glassman in U.S. Pat. No. 5,450,857 and Ramanajum et al in U.S. Pat. No. 5,421,339 have presented a method based on the use of fluorescence spectroscopy for the diagnosis of cancerous and pre-cancerous lesions of cervix. The main disadvantage of fluorescence spectroscopy is that the existing biochemical modifications associated with the progress of the disease are not manifested in a direct way as modifications in the measured fluorescence spectra. The fluorescence spectra contain limited diagnostic information of two basic reasons: a) Tissues contain non-fluorescent chromophores, such as hemoglobin. Absorption by such chromophores of the emitted light from fluorophores can result in artificial dips and peaks in the fluorescence spectra. In other words the spectra carry convoluted information for several components and therefore it is difficult to assess alterations in tissue features of diagnostic importance; and b) The spectra are broad due to the fact that a large number of tissue components are optically excited and contribute to the captured optical signal. As a result the spectra do not carry specific information for the pathologic alterations and thus they are of limited diagnostic value.

The latter is expressed as low sensitivity and specificity in the detection and classification of tissue lesions.

Aiming to enhance the sensitivity and specificity of the captured information, Ramanujan et al in the Patent No. WO 98/24369 have presented a method based on the use of neural networks for the analysis of the spectral data. This method is based on the training of a computing system with a large number of spectral patterns, which have been taken from normal and from pathologic tissues. The spectrum that is captured each time is compared with the stored spectral data, facilitating this way, the identification of the tissue pathology.

R. R. Kortun et al, in U.S. Pat. No. 5,697,373, seeking to improve the captured diagnostic information, have presented a method based on the combination of fluorescence spectroscopy and Raman scattering. The last has the capability of providing more analytical information, it requires however complex instrumentation and ideal experimental conditions, which substantially hinder their clinical use. It is generally known that tissues are characterized by the lack of spatial homogeneity and consequently the spectral analysis of distributed spatial points is insufficient for the characterization of their status.

Dombrowski in U.S. Pat. No. 5,424,543, describes a multi-wavelength, imaging system, capable of capturing tissue images in several spectral bands. With the aid of such a system it is possible in general to map characteristics of diagnostic importance based on their particular spectral characteristics. However, due to the insignificance of the spectral differences between normal and pathologic tissue, which is in general the case, inspection in narrow spectral bands does not allow the highlighting of these characteristics and even more so, the identification and staging of the pathologic area.

D. R. Sandison et al, in U.S. Pat. No. 5,920,399 describe an imaging system, developed for the in vivo investigation of cells, which combines multi-band imaging and light excitation of the tissue. The system also employs a dual fiber optic bundle for the transferring of the emitted from the source light onto the tissue and the remitted light from the tissue to the optical detector. These bundles are placed in contact with the tissue, and various wavelengths of excitation and imaging are combined in attempt to enhance the spectral differentiation between normal and pathologic tissue.

In U.S. Pat. No. 5,921,926, J. R. Delfyett et al have presented a method for the diagnosis of diseases of the cervix, which is based on the combination of Spectral Interferometry and Optical Coherence Tomography (OCT). This system combines three-dimensional imaging and spectral analysis of the tissue.

Moreover, several improved versions of colposcopes have been presented, (D. R. Craine et al, U.S. Pat. No. 5,791,346 and K. L. Blaiz U.S. Pat. No. 5,989,184) in most of which, electronic imaging systems have been integrated for image capturing, analysis of tissue images, including the quantitative assessment of lesion's size. For the enhancement of the optical differentiation between normal and pathologic tissue, special agents are used in various fields of biomedical diagnostics, which are administered topically or systematically. Such agents are acetic acid solution, toluidine blue, various photosensitizers (porphyrines) (S. Anderson Engels, C. Klinteberg, K. Svanberg, S. Svanberg, In vivo fluorescence imaging for tissue diagnostics, Phys Med. Biol. 42 (1997) 815-24). The provoked selective staining of the pathologic tissue is owed to the property of these agents to interact with the altered metabolic and structural characteristics of the pathologic area. This interaction enhances progressively and reversibly the differences in the spectral characteristics of reflection and/or fluorescence between normal and pathologic tissue. Despite the fact that the provoked selective staining of the pathologic tissue is a dynamic phenomenon, in clinical practice the intensity and the extent of the staining are assessed qualitatively and statically. Furthermore, in several cases of early pathologic conditions, the phenomenon of temporary staining after administering the agent, is short-lasting and thus the examiner is not able to detect the provoked alterations and even more so, to assess their intensity and extent. In other cases, the staining of the tissue progresses very slowly, with the consequence of patient discomfort and creation of problems for the examiner in assessing the intensity and extent of the alterations, since they are continuously changing. The above have as direct consequence, the downgrading of the diagnostic value of these diagnostic procedures and thus its usefulness is limited to facilitate the localization of suspected areas for obtaining biopsy samples.

Summarizing the above mentioned, the following conclusions are drawn:

a) Various conventional light dispersion spectroscopic techniques (fluorescence, elastic, non elastic scattering, etc) have been proposed and experimentally used for the in vivo detection of alterations in the structural characteristics of pathologic tissue. The main disadvantage of these techniques is that they provide point information, which is inadequate for the analysis of the spatially non-homogenous tissue. Multi-band imaging has the potential to solve this problem, by providing spectral information (of lesser resolution as a rule) but in any spatial point of the area under examination. These techniques (imaging and non-imaging) however, provide information of limited diagnostic value, due to the fact that the structural tissue alterations, which are accompanying the development of the disease, are not manifested as significant and characteristic alterations on the measured spectra. Consequently, the captured spectral information cannot be directly correlated with the tissue pathology, a fact which limits the clinical usefulness of these techniques.

b) The conventional (non-spectral) imaging techniques provide the capability of mapping characteristics of diagnostic importance in two or three dimensions. They are basically used for measuring morphological characteristics and as clinical documentation tools.

c) The diagnostic methods which are based on the selective staining of pathologic tissue with special agents allows the enhancement of the optical contrast between normal and pathologic tissue. Nevertheless they provide limited information for the in vivo identification and staging of the disease.

Given the fact that the selective interaction of pathologic tissue with the agents, which enhance its optical contrast with healthy tissue is a dynamic phenomenon, it is reasonable to suggest that the capture and analysis of the characteristics of this phenomenon's kinetics, could provide important information for the in vivo detection, identification and staging of tissue lesions. In a previous publication by the inventors (C. Balas, A. Dimoka, E. Orfanoudaki, E. Koumandakis, "In vivo assessment of acetic acid-cervical tissue interaction using quantitative imaging of back-scattered light: Its potential use for the in vivo cervical cancer detection grading and mapping", SPIE-Optical Biopsies and Microscopic Techniques, Vol. 3568 pp. 31-37, (1998)), measurements of the alterations in the characteristics of the back-scattered light as a function of wave-length and time are presented. These alterations are provoked in the cervix by the topical administration of acetic acid solution. In this particular case, there was used as an experimental apparatus, a general-purpose multi-spectral imaging system built around a tunable liquid crystal monochromator for measuring the variations in intensity of the back-scattered light as a function of time and wavelength in selected spatial points. It was found that the lineshapes of curves of intensity of back-scattered light versus time, provide advanced information for the direct identification and staging of tissue neoplasias. Unpublished results of the same research team support that similar results can also be obtained with other agents, which have the property of enhancing the optical contrast between normal and pathologic tissue. Nevertheless, the experimental method employed in the published paper is characterized by quite a few disadvantages, such as: The imaging monochromator requires time for changing the imaging wavelength and as a consequence it is inappropriate for multispectral imaging and analysis of dynamic phenomena. It does not constitute a method for the mapping of the grade of the tissue lesions, as the presented curves illustrate the temporal alterations of intensity of the back-scattered light in selected points. The lack of data modeling and parametric analysis of the characteristics of the phenomenon kinetics in any spatial point of the area of interest restrict the usefulness of the method in experimental studies and hinder its clinical implementation. The optics used for the imaging of the area of interest are of general purpose and do not comply with the special technical requirements for the clinical implementation of the method. Clinical implementation of the presented system is also hindered by the fact that it does not integrate appropriate means for ensuring the stability of the relative position between the tissue surface and image capturing module, during the snapshot imaging procedure. This is very important since small movements of the patient (i.e. breathing) are always present during the examination procedure. If micro-movements are taking place during successive capturing of images, after application of the agent, then the spatial features of the captured images are not coincide. This reduces substantially the precision in the calculation of the curves in any spatial point, that express the kinetics of marker-tissue interaction.

SUMMARY OF THE INVENTION

The present invention provides, at least in part, a method for monitoring the effects of a pathology differentiating agent on a tissue sample by applying a pathology differentiating agent, e.g., acetic acid, on a tissue sample and monitoring the rate of change of light reflection from the tissue sample over time, thereby monitoring the effects of a pathology differentiating agent on a tissue sample. The tissue may be a cervical, ear, oral, skin, esophagus, or stomach tissue. Without intending to be limited by theory, it is believed that the pathology differentiating agent provokes transient alterations in the light scattering properties of the tissue, e.g., the abnormal epithelium.

In another aspect, the present invention features a method for the in vivo diagnosis of a tissue abnormality, e.g., a tissue atypia, a tissue dysplasia, a tissue neoplasia (such as a cervical intraepithelial neoplasia, CINI, CINII, CINIII) or cancer, in a subject. The method includes contacting a tissue in a subject with a pathology differentiating agent, e.g., an acetic acid solution or a combination of solutions selected from a plurality of acidic and basic solutions, exposing the tissue in the subject to optical radiation; and monitoring the intensity of light emitted from the tissue over time, thereby diagnosing a tissue abnormality in a subject. The optical radiation may be broad band optical radiation, preferably polarized optical radiation.

The non-invasive methods of the present invention are useful for the in vivo early detection of tissue abnormalities/alterations and mapping of the grade of these tissue abnormalities/alterations, caused in the biochemical and/or in the functional characteristics of epithelial tissues, during the development of tissue atypias, dysplasias, neoplasias and cancers.

In one embodiment, the tissue area of interest is illuminated with a broad band optical radiation and contacted with a pathology differentiating agent, e.g., an agent or a combination of agents which interact with pathologic tissue areas characterized by an altered biochemical composition and/or cellular functionality and provoke a transient alteration in the characteristics of the light that is re-emitted from the tissue. The light that is re-emitted from the tissue may be in the form of reflection, diffuse scattering, fluorescence or combinations or subcombinations thereof. The intensity of the light emitted from the tissue may be measured, e.g., simultaneously, in every spatial point of the tissue area of interest, at a given time point or over time (e.g., for the duration of agent-tissue interaction). A diagnosis may be made based on the quantitative assessment of the spatial distribution of alterations in the characteristics of the light re-emitted from the tissue at given time points, before and after the optical and chemical excitation of the tissue and/or based on the quantitative assessment of the spatial distribution of parameters, calculated from the characteristic curves that express the kinetics of the provoked alterations in the characteristics of the light re-emitted from the tissue, which characteristic curves are simultaneously measured in every spatial point of the area under examination during the optical and chemical excitation of the tissue.

In one embodiment of the invention, the step of tissue illumination comprises exposing the tissue area under analysis to optical radiation of narrower spectral width than the spectral width of the light emitted by the illumination source. In another embodiment, the step of measuring the intensity of light comprises measuring the intensity of the re-emitted light in a spectral band, the spectral width of which is narrower than the spectral width of the detector's sensitivity. In yet another embodiment, the step of measuring the intensity of light comprises measuring simultaneously the intensity of the re-emitted light in a plurality of spectral bands, the spectral widths of which are narrower than the spectral width of the detector's sensitivity.

In yet another aspect, the present invention features an apparatus for the in vivo, non-invasive early detection of tissue abnormalities/alterations and mapping of the grade of these tissue abnormalities/alterations, caused in the biochemical and/or in the functional characteristics of epithelial tissues, during the development of tissue atypias, dysplasias, neoplasias and cancers. The apparatus includes optics for collecting the light re-emitted by the area under analysis, selecting magnification and focusing the image of the area; optical imaging detector(s); means for the modulation, transfer, display and capturing of the image of the tissue area of interest; a computer which includes data storage, processing and analysis means; a monitor for displaying images, curves and numerical data; optics for the optical multiplication of the image of the tissue area of interest; a light source for illuminating the area of interest; optionally, optical filters for selecting the spectral band of imaging and illumination; means for transmitting light and illuminating the area of interest; control electronics; and optionally, software for the analysis and processing of data, which also enables the tissue image capturing and storing in specific time points and for a plurality of time points, before and after administration of the pathology differentiating agent.

Using the foregoing apparatus an image or a series of images may be created which express the spatial distribution of the characteristics of the kinetics of the provoked changes in the tissue's optical characteristics, before and after the administration of the agent, with pixel values corresponding with the spatial distribution of the alterations in the intensity of the light emitted from the tissue, in given time instances, before and after the optical and chemical excitation of tissue and/or with the spatial distribution of parameters derived from the function: pixel gray value versus time. The foregoing function may be calculated from the captured and stored images and for each row of pixels with the same spatial coordinates.

In one embodiment, the step of optical filtering the imaging detector comprises an optical filter that is placed in the optical path of the rays that form the image of the tissue, for the recording of temporally successive images in a selected spectral band, the spectral width of which is narrower than the spectral width of the detector's sensitivity.

In yet another embodiment, the image multiplication optics comprise light beam splitting optics that create two identical images of the area of interest, which are recorded by two imaging detectors, in front of which optical filters are placed, with in general different transmission characteristics and capable of transmitting light of spectral width shorter than the spectral width of the detector's sensitivity, so that two groups of temporally successive images of the same tissue area are recorded simultaneously, each one corresponding to a different spectral band.

In another embodiment, the image multiplication optics comprise more than one beam splitter for the creation of multiple identical images of the area of interest, which are recorded by multiple imaging detectors, in front of which optical filters are placed, with, preferably, different transmission characteristics and capable of transmitting light of spectral width shorter than the spectral width of the detector's sensitivity, so that multiple groups of temporally successive images of the same tissue area are recorded simultaneously, each one corresponding to a different spectral band.

In a further embodiment, the image multiplication optics comprise one beam splitter for the creation of multiple identical images of the area of interest, which are recorded by multiple imaging detectors, in front of which optical filters are placed with, preferably, different transmission characteristics and capable of transmitting light of spectral width shorter than the spectral width of the detector's sensitivity, so that multiple groups of temporally successive images of the same tissue area are recorded simultaneously, each one corresponding to a different spectral band.

In yet a further embodiment, the image multiplication optics comprise one beam splitter for the creation of multiple identical images of the area of interest, which are recorded in different sub-areas of the same detector, and in front these areas optical filters are placed with, preferably, different transmission characteristics and capable of transmitting light of spectral width shorter than the spectral width of the detector's sensitivity, so that multiple groups of temporally successive images of the same tissue area are recorded simultaneously in the different areas of the detector, each one corresponding to a different spectral band.

In another embodiment, the step of filtering the light source comprises an optical filter, which is placed in the optical path of an illumination light beam, and transmits light of spectral width shorter than the spectral width of sensitivity of the detector used.

In a further embodiment, the step of filtering the light source comprises a plurality of optical filters and a mechanism for selecting the filter that is interposed to the tissue illumination optical path, thus enabling the tuning of the center wavelength and the spectral width of the light illuminating the tissue.

In another embodiment, the mapping of the grade of the alterations to the biochemical and/or functional characteristics of the tissue area of interest, is based on the pixel values of one image, from the group of the recorded temporally successive images of the tissue area of interest.

In a further embodiment, the mapping of the grade of the alterations to the biochemical and/or functional characteristics of the tissue area of interest, is based on the pixel values belonging to plurality of images, which are members of the group of the recorded temporally successive images of the tissue area of interest.

In another embodiment, the mapping of the grade of the alterations to the biochemical and/or functional characteristics of the tissue area of interest, is based on numerical data derived from mathematical operations and calculations between the pixel values belonging a plurality of images, which are members of the group of the recorded temporally successive images of the tissue area of interest.

In a further embodiment, a pseudo-color scale, which represents with different colors the different pixel values of the image or of the images used for the mapping of abnormal tissue areas, is used for the visualization of the mapping of the grade of the alterations to the biochemical and/or functional characteristics of the tissue area under examination.

In one embodiment, the image or images which are determined for the mapping of the grade of the alterations in biochemical and/or functional characteristics of tissue, are used for the in vivo detection, mapping, as well as for the determination of the borders of epithelial lesions.

In another embodiment, the pixel values of the image or of the images which are determined for the mapping of the grade of alterations in biochemical and/or functional characteristics of tissue, are used as diagnostic indices for the in vivo identification and staging of epithelial lesions.

In yet another embodiment, the image or the images which are determined for the mapping of the grade of the alterations in biochemical and/or functional characteristics of tissue can be overimposed onto the color or black and white image of the same area of tissue under examination displayed on the monitor, so that abnormal tissue areas are highlighted and their borders are demarcated, facilitating the selection of a representative area for taking a biopsy sample, the selective surgical removal of the abnormal area and the evaluation of the accuracy in selecting and removing the appropriate section of the tissue.

In a further embodiment, the image or the images which are determined for the mapping of the grade of alterations in biochemical and/or functional characteristics of tissue are used for the evaluation of the effectiveness of various therapeutic modalities such as radiotherapy, nuclear medicine treatments, pharmacological therapy, and chemotherapy.

In another embodiment, the optics for collecting the light re-emitted by the area under analysis, comprises the optomechanical components employed in microscopes used in clinical diagnostic examinations, surgical microscopes, colposcopes and endoscopes.

In one embodiment of the invention, for colposcopy applications, the apparatus may comprise a speculum, an articulated arm onto which the optical head is attached, which optical head comprises a refractive objective lens, focusing optics, a mechanism for selecting the magnification, an eyepiece, a mount for attaching a camera, and an illuminator, where the speculum is attached in a fixed location onto the system articulated arm-optical head, in such a way such that the central longitudinal axis of the speculum is perpendicular to the central area of the objective lens, so that when the speculum is inserted into the vagina and fixed in it, the relative position of the image-capturing optics and of the tissue area of interest remains unaltered, regardless of micro-movements of the cervix, which are taking place during the examination of the female subject.

In a further embodiment, the apparatus may further comprise an atomizer for delivering the agent, where the atomizer is attached in a fixed point onto the system articulated arm-optical head of the apparatus and in front of the vaginal opening, where the spraying of the tissue may be controlled and synchronized with a temporally successive image capturing procedure, with the aid of electronic control means.

In another embodiment of the apparatus of the invention, the image capturing detector means and image display means comprise a camera system with detector spatial resolution greater than 1000×1000 pixels and a monitor of at least 17 inches (diagonal), so that high magnification is ensured together with a large field of view, while the image quality is maintained.

In a further embodiment, in the case of microscopes used in clinical diagnostic examinations, surgical microscopes and colposcopes, comprise an articulated arm onto which the optical head is attached, which optical head comprises an objective lens, focusing optics, a mechanism for selecting the magnification, an eyepiece, a mount for attaching a camera, an illuminator and two linear polarizers, where the two linear polarizers are attached, one at a point along the optical path of the illuminating light beam and the other at a point along the optical path of the rays that form the image of the tissue, with the capability of rotating the polarization planes of these light polarizing optical elements, so that when these planes are perpendicular to each other, the contribution of the tissue's surface reflection to the formed image is eliminated.

In another embodiment, in the case of endoscopy, the endoscope may comprise optical means for transferring light from the light source onto the tissue surface and for collecting and transferring along almost the same axis and focusing the rays that form the image of the tissue, and two linear polarizers, where the two linear polarizers are attached, one at a point along the optical path of the illuminating light beam and the other at a point along the optical path of the rays that form the image of the tissue, with the capability of rotating the polarization planes of these light polarizing optical elements, so that when these planes are perpendicular to each other, the contribution of the tissue's surface reflection to the formed by the endoscope image is eliminated.

In another embodiment, in the case of microscopes used in clinical diagnostic examinations, surgical microscopes and colposcopes, may additionally comprise a reflective objective lens, where the reflective objective replaces the refractive one, which reflective objective is devised so that in the central part of its optical front aperture the second reflection mirror is located, and in the rear part (non-reflective) of this mirror, illumination means are attached from which light is emitted toward the object, so that with or without illumination beam zooming and focusing optics the central ray of the emitted light cone is coaxial, with the central ray of the light beam that enters the imaging lens, and with the aid of zooming and focusing optics of illumination beam that may be adjusted simultaneously and automatically with the mechanism for varying the magnification of the optical imaging system, the illuminated area and the field-of-view of the imaging system, are varying simultaneously and proportionally, so that any decrease in image brightness caused by increasing the magnification, is compensated with the simultaneous zooming and focusing of the illumination beam.

Other features and advantages of the invention will be apparent from the following detailed description and claims.

DETAILED DESCRIPTION OF THE INVENTION

Figure 1A:
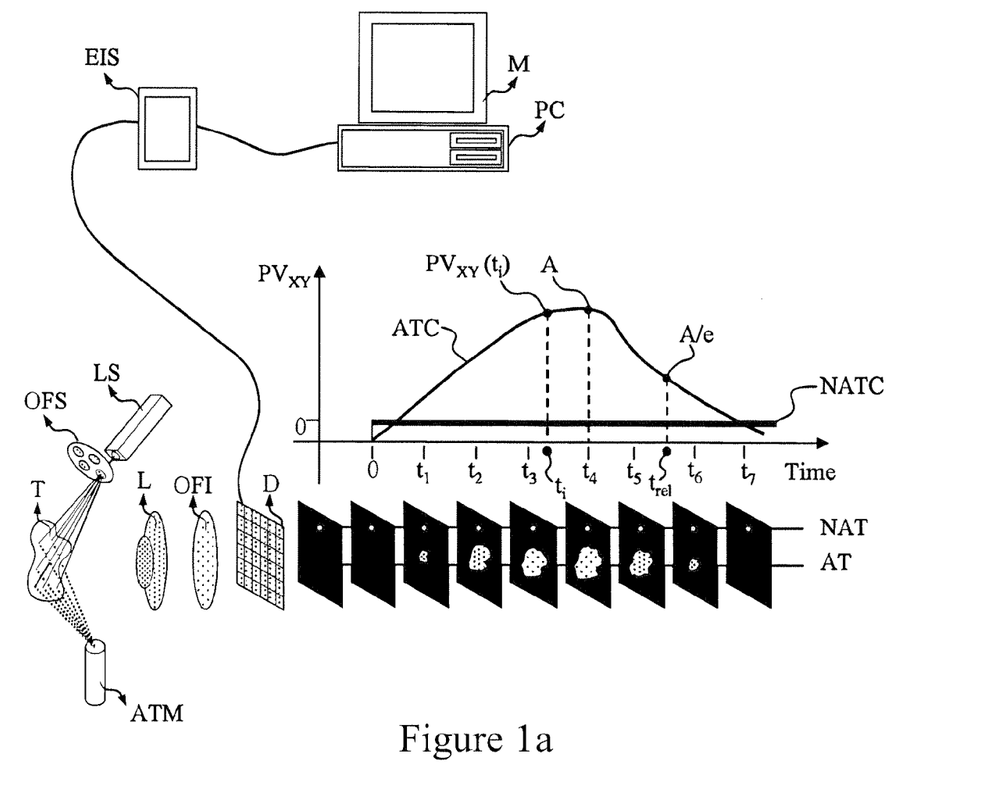
FIGS. 1a and 1b are a schematic representation of the present method's basic principle.

The present invention is directed to a method and system for the in-vivo, non-invasive detection and mapping of the biochemical and or functional alterations of tissue, e.g., tissue within a subject. Upon selection of the appropriate agent which enhances the optical contrast between normal and pathologic tissue (depending on the tissue's pathology), this agent is administered, e.g., topically to the tissue. In FIG. 1, the tissue (T), is sprayed using an atomizer (A), which contains the agent, e.g., acetic acid. At the same time, the tissue is illuminated with a source that emits light at a specific spectral band, depending on the optical characteristics of both the agent and the tissue. Illumination and selection of the spectral characteristics of the incident to the tissue light can be performed with the aid of a light source (LS) and a mechanism for selecting optical filters (OFS). Of course there are several other methods for illuminating the tissue and for selecting the spectral characteristics of the incident light (e.g., Light emission diodes, LASERS and the like).

For the imaging of the area of interest, light collection optics (L) are used, which focus the image onto a two-dimensional optical detector (D). The output signal of the latter is amplified, modulated and digitized with the aid of appropriate electronics (EIS) and finally the image is displayed on a monitor (M) and stored in the data-storing means of a personal computer (PC). Between tissue (T) and detector (D), optical filters (OFI) can be interposed. The interposition of the filter can be performed for tissue (T) imaging in selected spectral bands, at which the maximum contrast is obtained between areas that are subjected to different grade of alterations in their optical characteristics, provoked after administering the appropriate agent.

Before administration of the latter, images can be captured and used as reference. After the agent has been administered, the detector (D), captures images of the tissue, in successive time instances, which are then stored in the computer's datastorage means. The capturing rate is proportional to the rate at which the tissue's optical characteristics are altered, following the administration of the agent.

Figure 1B:
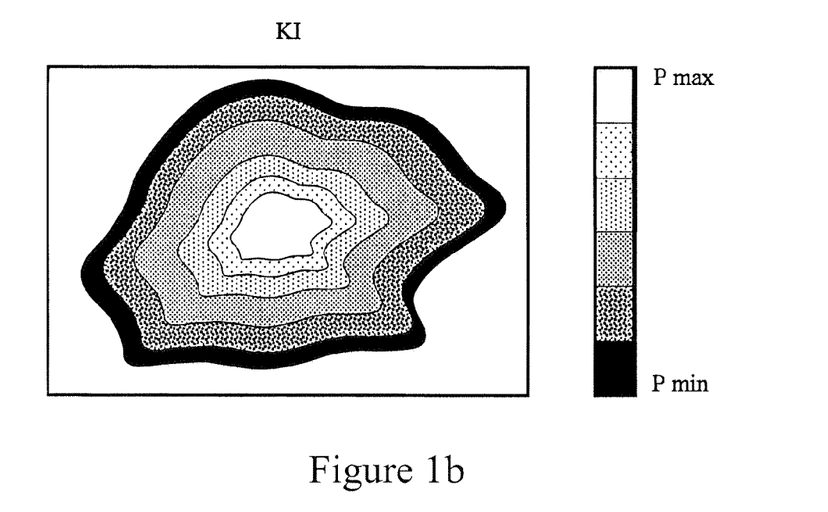

In FIG. 1b, images of the same tissue area are schematically illustrated, which have been stored successively before and after administering the agent (STI). In these images, the black areas represent tissue areas that do not alter their optical characteristics (NAT), while the gray-white tones represent areas which alter their optical characteristics (AT), following the administration of the agent. The simultaneous capture of the intensity of the light re-emitted from every spatial point of the tissue area under analysis and in predetermined time instances, allows the calculation of the kinetics of the provoked alterations.

In FIG. 1a, two curves are illustrated: pixel value in position xy (Pvxy), versus time t. The curve ATC corresponds to an area where agent administration provoked alterations (AT) in the tissue's optical characteristics. The curve (NATC) corresponds to an area where no alteration took place (NAT).

The mathematical analysis of these curves, leads to the calculation of quantitative parameters for every pixel such as: The value PVxy that corresponds to the time ti, the relaxation time trel which corresponds to the value Pvxy=A/e (where e is the base of Neper logarithms), etc.

The calculation of these parameters (P) in every spatial point of the area under analysis, allows the calculation of the image or images of the kinetics of the phenomenon (KI), with pixel values that are correlated with these parameters. These values can be represented with a scale of pseudocolors (Pmin, Pmax), the spatial distribution of which allows for immediate optical evaluation of the intensity and extent of the provoked alterations. Depending on the correlation degree between the intensity and the extent of the provoked alterations with the pathology and the stage of the tissue lesion, the measured quantitative data and the derived parameters would allow the mapping, the characterization and the border-lining of the lesion. The pseudocolor image of the phenomenon's kinetics (KI), which expresses the spatial distribution of one or more parameters, can be superimposed (after being calculated) on the tissue image, which is displayed in real-time on the monitor. The using the superimposed image as a guide, facilitates substantially the determination of the lesion's boundaries, for successful surgical removal of the entire lesion, or for locating suspicious areas in order to obtain a biopsy sample(s). Furthermore, based on the correlation of the phenomenon's kinetics with the pathology of the tissue, the measured quantitative data and the parameters that derive from them, can constitute quantitative clinical indices for the in vivo staging of the lesion or of sub-areas of the latter.

In some cases it is necessary to capture the kinetics of the phenomenon in more than one spectral band. This can serve in the in vivo determination of illumination and/or imaging spectral bands at which the maximum diagnostic signal is obtained. Furthermore, the simultaneous imaging in more than one spectral band can assist in minimizing the contribution of the unwanted endogenous scattering, fluorescence and reflection of the tissue, to the optical signal captured by the detector. The captured optical signal comprises the optical signal generated by the marker-tissue interaction and the light emitted from the endogenous components of the tissue. In many cases the recorded response of the components of the tissue constitutes noise, since it occludes the generated optical signal, which carries the diagnostic information. Therefore, separation of the above optical signals, based on their particular spectral characteristics, will result in the maximization of the signal-to-noise ratio and consequently in the improvement of the obtained diagnostic information.

Figure 2:
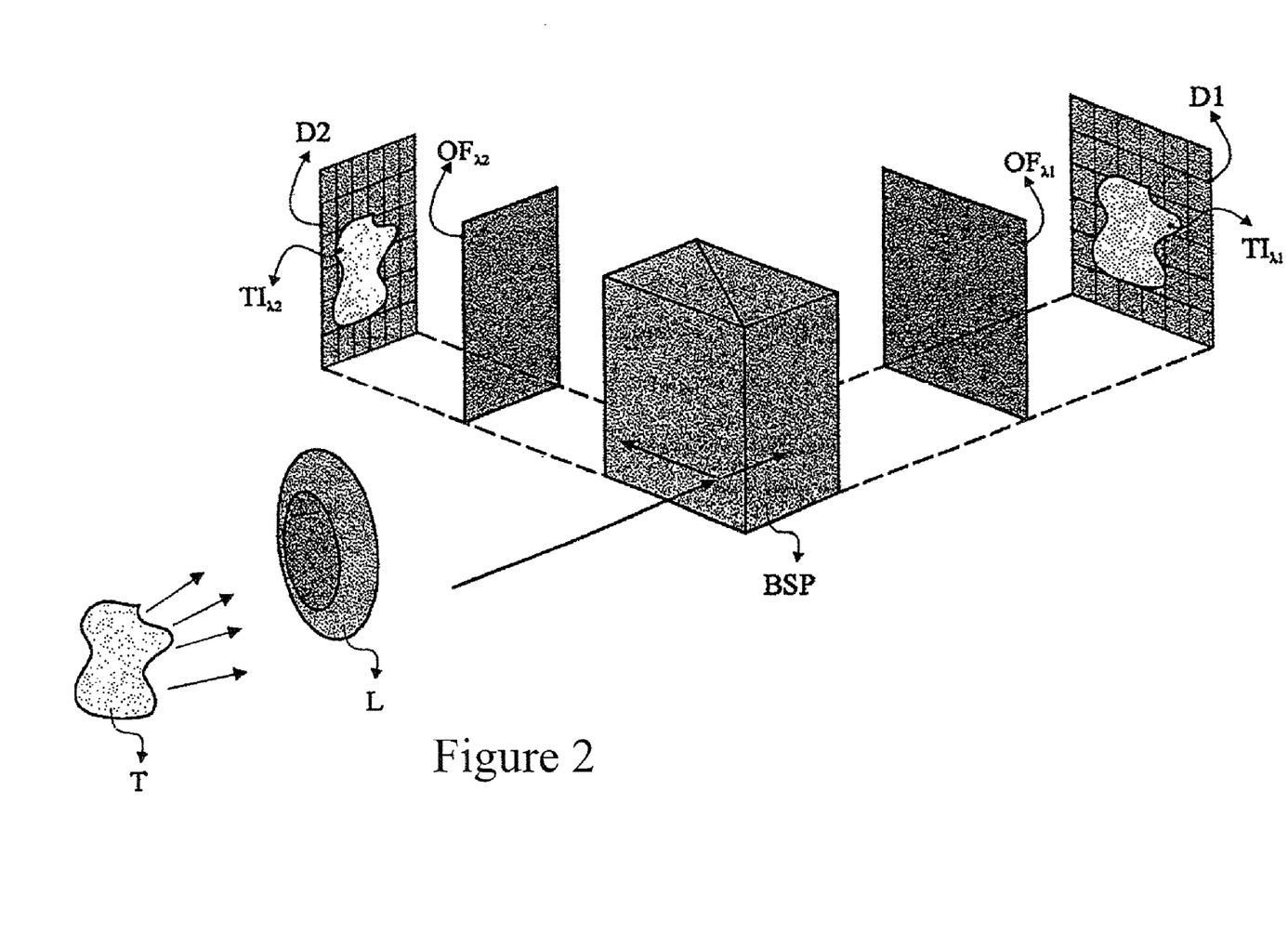
FIG. 2, illustrates an embodiment of the invention comprising a method for capturing in two spectral bands simultaneously and in any spatial point of the area under analysis, the kinetics of the alterations in the characteristics of the remitted from the tissue light, before and the after the administration of the contrast enhancing agent

FIG. 2, illustrates a method for capturing in two spectral bands simultaneously and in any spatial point of the area under analysis, the kinetics of the alterations in the characteristics of the remitted from the tissue light, before and the after the administration of the contrast enhancing agent. The remitted from the tissue light, is collected and focused by the optical imaging module (L) and passes through a beam splitting (BSP) optical element. Thus, two identical images of the tissue (T) are generated, which can be captured by two detectors (D1, D2). In front of the detector, appropriate optical filters (Ofλ1), (Ofλ2) can be placed, so that images with different spectral characteristics are captured. Besides beam splitters, optical filters, dichroic mirrors etc, can also be used for splitting the image of the object. The detectors (D1), (D2) are synchronized so that they capture simultaneously the corresponding spectral images of the tissue (Tiλ1), (Tiλ2) and in successive time-intervals, which are stored in the computer's data storage means. Generalizing, multiple spectral images can be captured simultaneously by combining multiple splitting elements, filters and sources.

Figure 3:
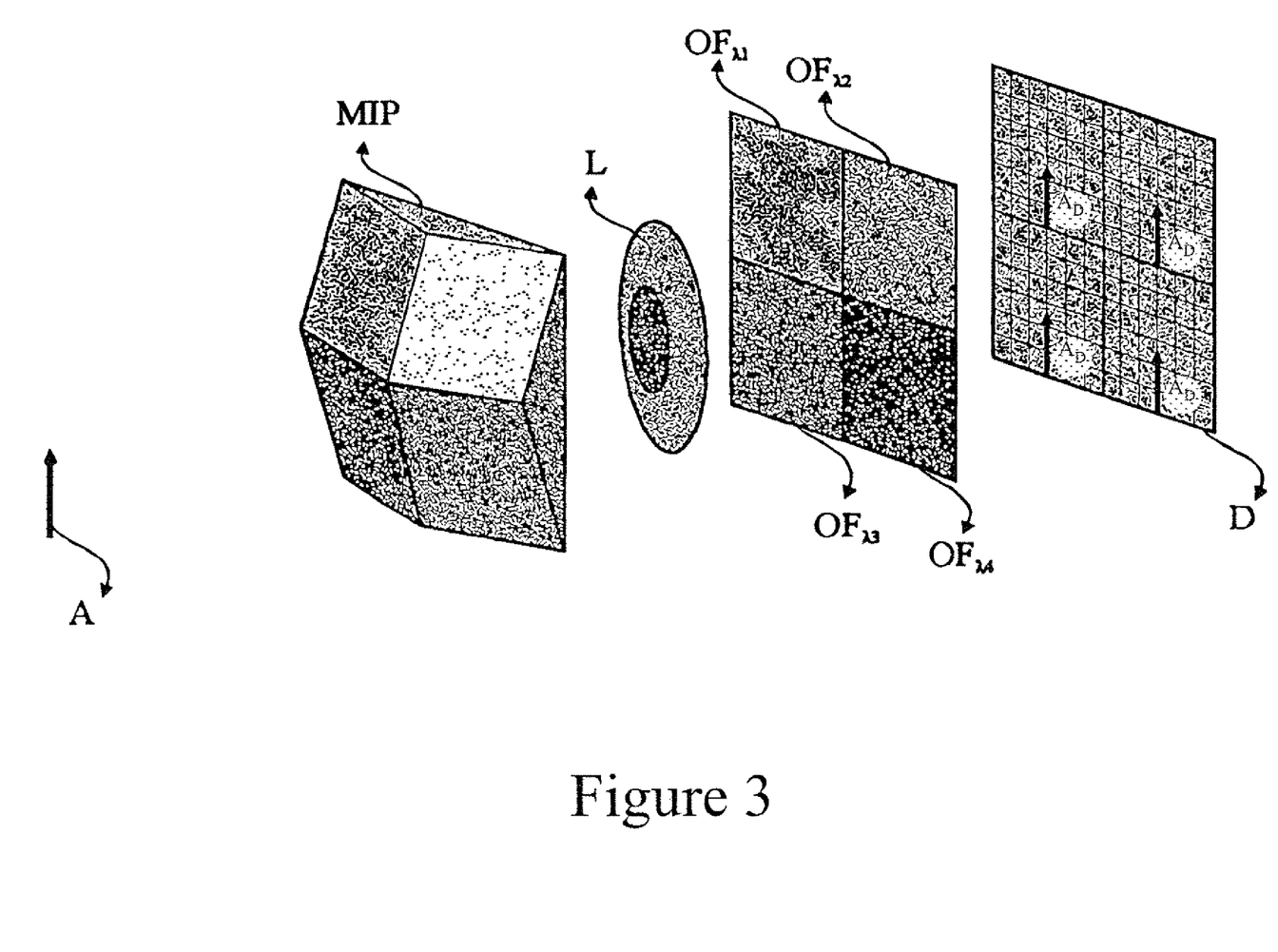
FIG. 3 illustrates another embodiment of the invention comprising a method for capturing in different spectral bands simultaneously and in any spatial point of the area under analysis, the kinetics of the alterations in the characteristics of the remitted from the tissue light, before and the after the administration of the contrast enhancing agent.

FIG. 3 illustrates another method for capturing in different spectral bands simultaneously and in any spatial point of the area under analysis, the kinetics of the alterations in the characteristics of the remitted from the tissue light, before and the after the administration of the contrast enhancing agent. With the aid of a special prism (MIP) and imaging optics, it is possible to form multiple copies of the same image onto the surface of the same detector (D). Various optical filters (OFλ1),(OFλ2),(OFλ3),(OFλ4), can be interposed along the length of the optical path of the rays that form the copies of the object's image, so that the captured multiple images correspond to different spectral areas.

For the clinical use of the methods of the invention, the different implementations of image capturing module described above can be integrated to conventional optical imaging diagnostic devices. Such devices are the various medical microscopes, colposcopes and endoscopes, which are routinely used for the in vivo diagnostic inspection of tissues. Imaging of internal tissues of the human body requires in most cases the illumination and imaging rays to travel along the same optical path, through the cavities of the body. Due to this fact, in the common optical diagnostic devices the tissue's surface reflection contributes substantially in the formed image. This limits the imaging information for the subsurface characteristics, which are in general of great diagnostic importance. This problem becomes more serious especially in epithelial tissues such as the cervix, larynx, oral cavity etc, which are covered by fluids such as mucus and saliva. Surface reflection also obstructs the detection and the measurement of the alterations in the tissue's optical properties, provoked after the administration of agents which enhance the optical contrast between normal and pathologic tissue. More specifically, when a special agent alters selectively the scattering characteristics of the pathologic tissue, the strong surface reflection that takes place in both pathologic (agent responsive) and normal (agent non responsive) tissue areas, occludes the diagnostic signal that originates from the interaction of the agent with the subsurface features of the tissue. In other words, surface reflection constitutes optical noise in the diagnostic signal degrading substantially the perceived contrast between agent responsive and agent non responsive tissue areas.

Figure 4:
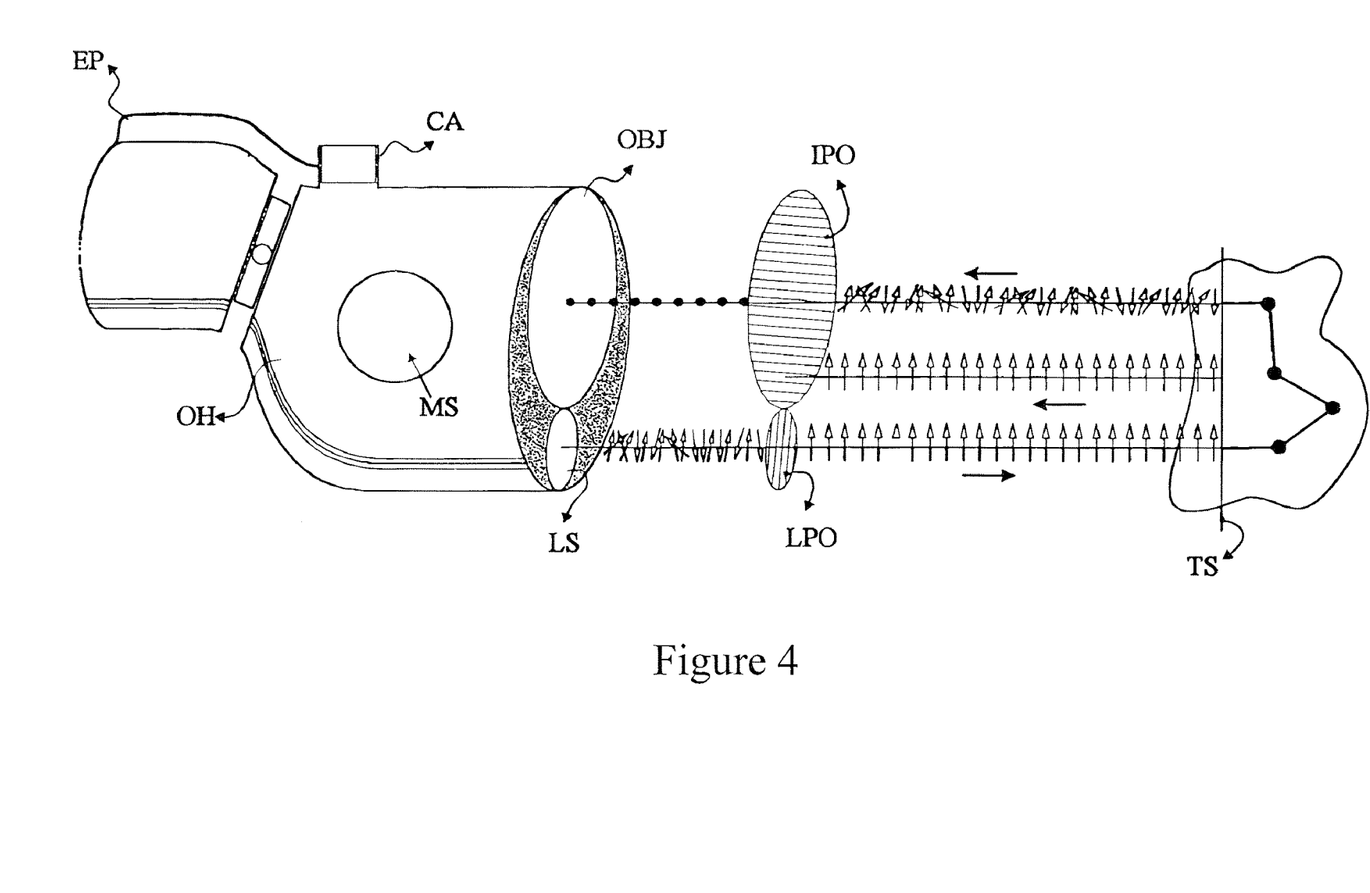
FIG. 4 illustrates a schematic diagram of a medical microscope comprising a light source (LS), a magnification selection mechanism (MS), an eyepiece (EP) and a mount for attaching the image capturing module (CA), (detector(s), readout electronics etc).

Based on the above, the effective integration of the method to imaging diagnostic devises devices, requires embodiments of appropriate optics that ensure the elimination of the contribution of surface reflection to the captured image. FIG. 4 illustrates a schematic diagram of a medical microscope consisting a light source (LS), a magnification selection mechanism (MS), an eyepiece (EP) and a mount for attaching the image capturing module (CA), (detector(s), readout electronics etc). For the elimination of the surface reflection a pair of linear polarizers is employed. The incident to the tissue light (LS), is linearly polarized by passing though a linear polarizer (LPO). The surface reflected light (TS), has the same polarization plane with the incident to the tissue light (Fresnel reflection). By interposing the other linear polarizer to the optical path of the rays that are remitted from the tissue and from the optical image of the object, with its polarization plane perpendicular to the polarization level of the incident to the tissue light (IPO), the contribution of the surface reflection to the image of the object is eliminated. The light which is not surface-reflected enters the tissue, where due to multiple scattering, light polarization is randomized. Thus, a portion of the re-emitted light passes through the imaging polarization optics, carrying improved information for the subsurface features.

Figure 5:
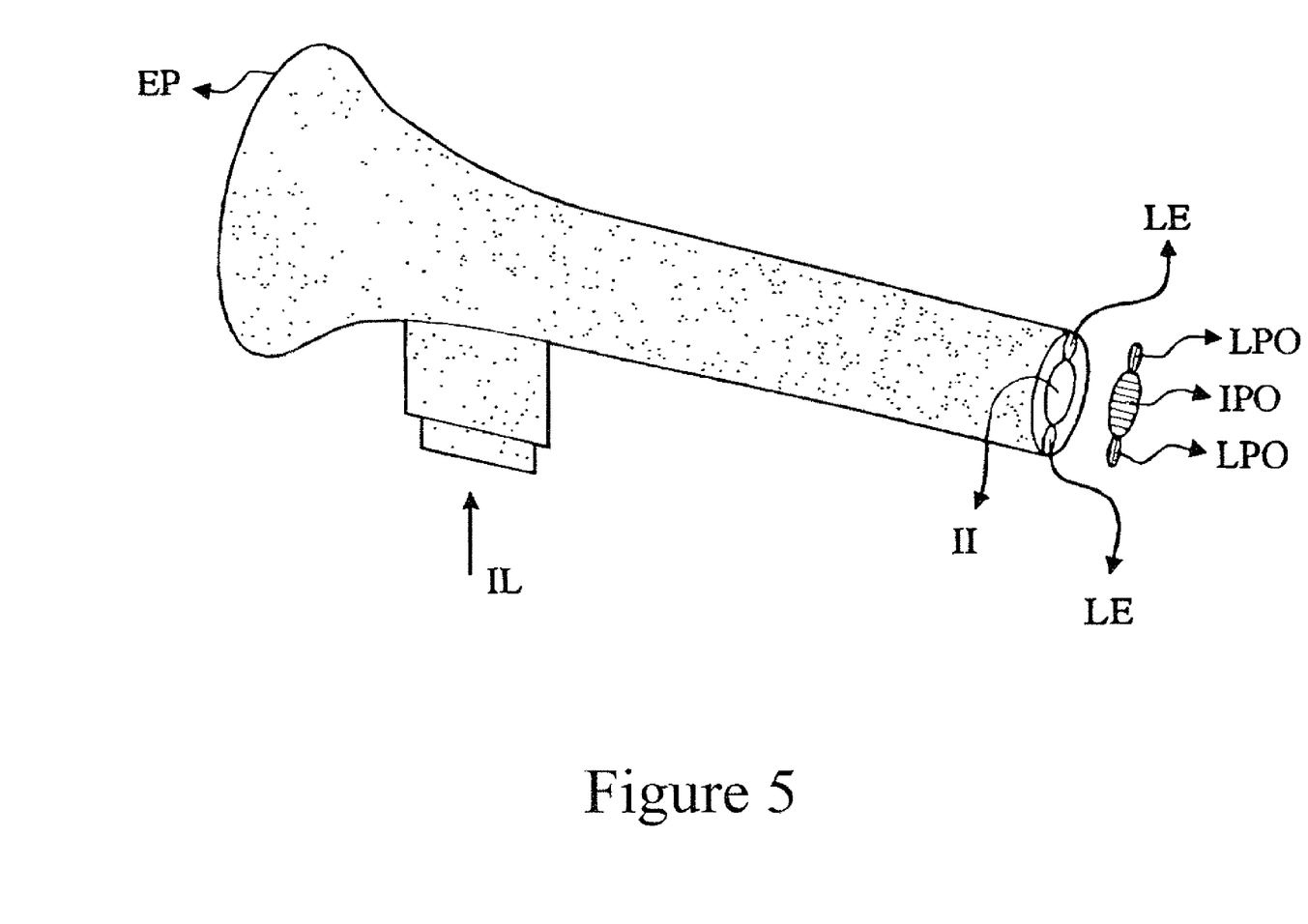
FIG. 5 illustrates an endoscope comprising an eyepiece (EP), which can be adapted to an electronic imaging system, optical fibers or crystals for the transmission of both illumination and image rays, optics for the linear polarization of light, one interposed to the optical path of the illumination rays (LE) and one to the path of the ray that form the optical image of the tissue (II).

FIG. 5 illustrates an endoscope consisting an eyepiece (EP), which can be used with an electronic imaging system, optical fibers or crystals for the transmission of both illumination and image rays, optics for the linear polarization of light, one interposed to the optical path of the illumination rays (LE) and one to the path of the ray that form the optical image of the tissue (II). The polarization plane of the polarizing optics, which are adapted to the exit of light from the endoscope (LPO), is perpendicular to the polarization plane of the polarizer, which is adapted to the point where the light enters the endoscope (IL). The polarization optics of the incident to the tissue light could also be adapted at the point where the light enters the endoscope (IL) but in this case, the endoscope has to be constructed using polarization preserving crystals or fiber optics for transferring the light. If polarization preserving light transmission media are used, then the polarizing optics of the imaging rays can be interposed in their path and before or after the eyepiece (EP).

A problem for the effective clinical implementation of the described method herein is the micro-movements of the patient, which are always present during the snapshot imaging of the same tissue area. Obviously this problem is eliminated in case that the patient is under anesthesia (open surgery). In most cases however the movements of the tissue relative to the image capturing module, occurring during the successive image capturing time-course, have the consequence that the image pixels, with the same image coordinates, do not correspond to exactly the same spatial point x,y of the tissue area under examination.

Figure 6:
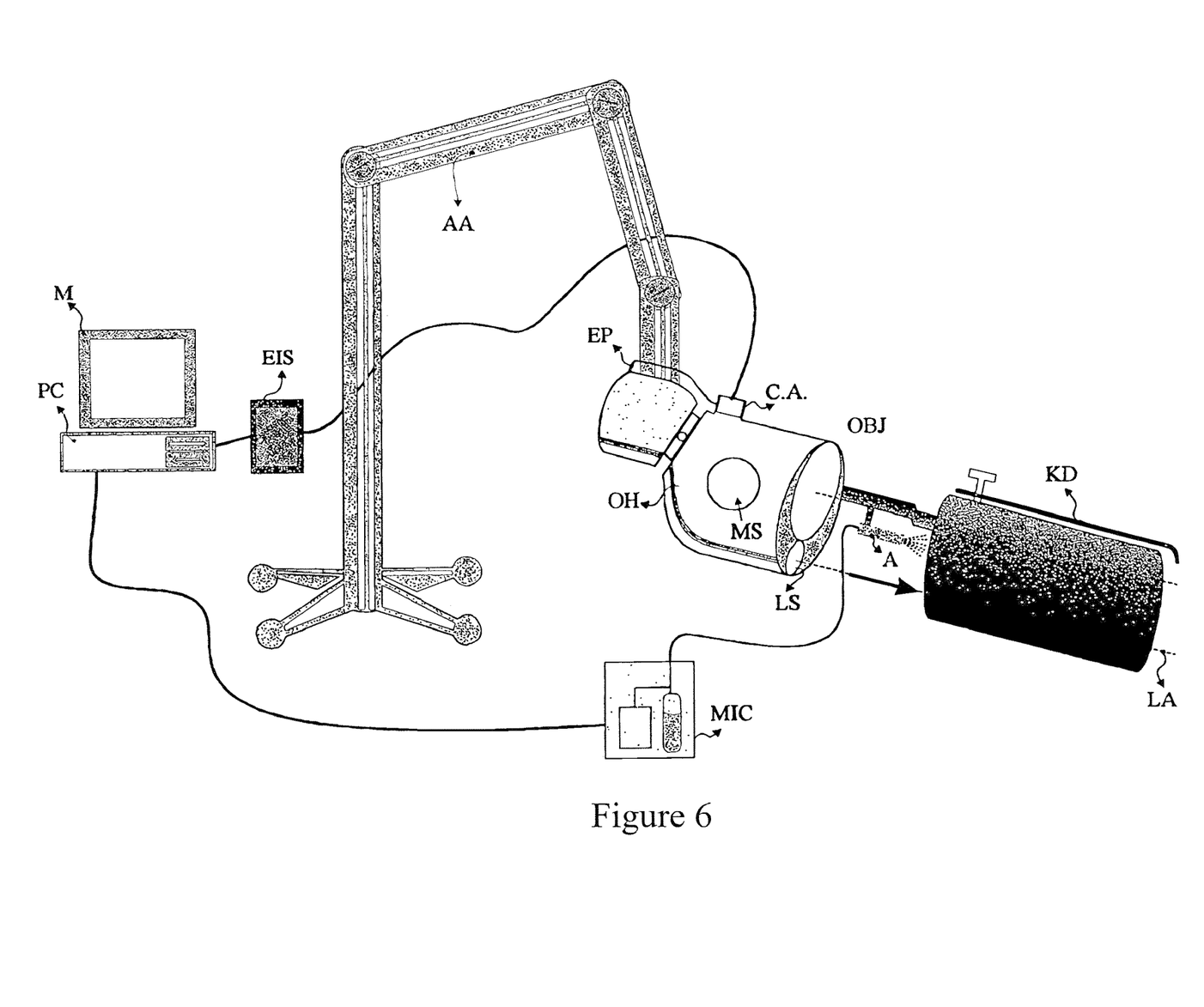
FIG. 6 depicts a colposcopic apparatus comprising an articulated arm (AA), onto which the optical head (OH) is affixed, which includes a light source (LS), an objective lens (OBJ), an eye-piece (EP) and optics for selecting the magnification (MS).

This problem is typically encountered in colposcopy. A method to eliminate the influence to the measured temporal data of the relative movements between tissue and image capturing module is presented below. A colposcopic apparatus is illustrated in FIG. 6, consisting an articulated arm (AA), onto which the optical head (OH) is affixed, which includes a light source (LS), an objective lens (OBJ), an eye-piece (EP) and optics for selecting the magnification (MS). The image capturing module is attached to the optical head (OH), through an opto-mechanical adapter. A speculum (KD), which is used to open-up the vaginal canal for the visualization of the cervix, is connected mechanically with the optical head (OH), so that the its longitudinal symmetry axis (LA), to be perpendicular to the central area of the objective lens (OBJ). The speculum enters the vagina and its blades are opened up compressing the side walls of the vagina. The Speculum (KD), been mechanically connected with the optical head (OH), transfer any micromovement of the patient to the optical head (OH), which been mounted on an articulated arm (AA), follows these movements. Thus the relative position between tissue and optical head remains almost constant.

An important issue that must also be addressed for the successful clinical implementation of the diagnostic method described herein, is the synchronization of the application of the contrast enhancing agent with the initiation of the snapshot imaging procedure. FIG. 6, illustrates an atomizer (A) attached to the optical head of the microscope. The unit (MIC) is comprised of electronics for controlling the agent sprayer and it can incorporate also the container for storing the agent. When the unit (MIC) receives the proper command from the computer it sprays a predetermined amount of the agent onto the tissue surface, while the same or another command initiates the snapshot image capturing procedure.

The diagnostic examination of non-directly accessible tissues, located in cavities of the human body (ear, cervix, oral cavity, esophagus, colon, stomach), is performed with the aid of common clinical microscopes. In these devices the illumination-imaging rays are near co-axial. More specifically, the line perpendicular to the exit point of light into the air, and the line perpendicular to the objective lens, form an angle of a few degrees. Due to this fact, these microscopes operate at a specific distance from the subject (working distance), in which the illuminated tissue area, coincides with the field-of-view of the imaging system. These microscopes are found to be inappropriate in cases where tissue imaging through human body cavities of small diameter and at short working distances, is required. These technical limitations also constitute serious restricting factors for the successful clinical implementation of the method described herein. As it has been discussed above, elimination of surface reflection results in a substantial improvement of the diagnostic information, obtained from the quantitative assessment of marker-tissue interaction kinetics. If a common clinical microscope is employed as the optical imaging module, then due the above mentioned Illumination-imaging geometry, multiple reflections are occurring in the walls of the cavity, before the light reaches the tissue under analysis. In the case of colposcopy, multiple reflections are much more intense, since they are mainly taking place onto highly reflective blades of the speculum. Recall that the latter is inserted into the vagina to facilitate the inspection of cervix.

If the illuminator of the imaging apparatus emits linearly polarized light, the multiple reflections are randomizing the polarization plane of the incident light. And as it has been discussed above, if the incident to the tissue under analysis light is not linearly polarized, then the elimination of the contribution of the surface reflection to the captured image can not be effective.

Figure 7:
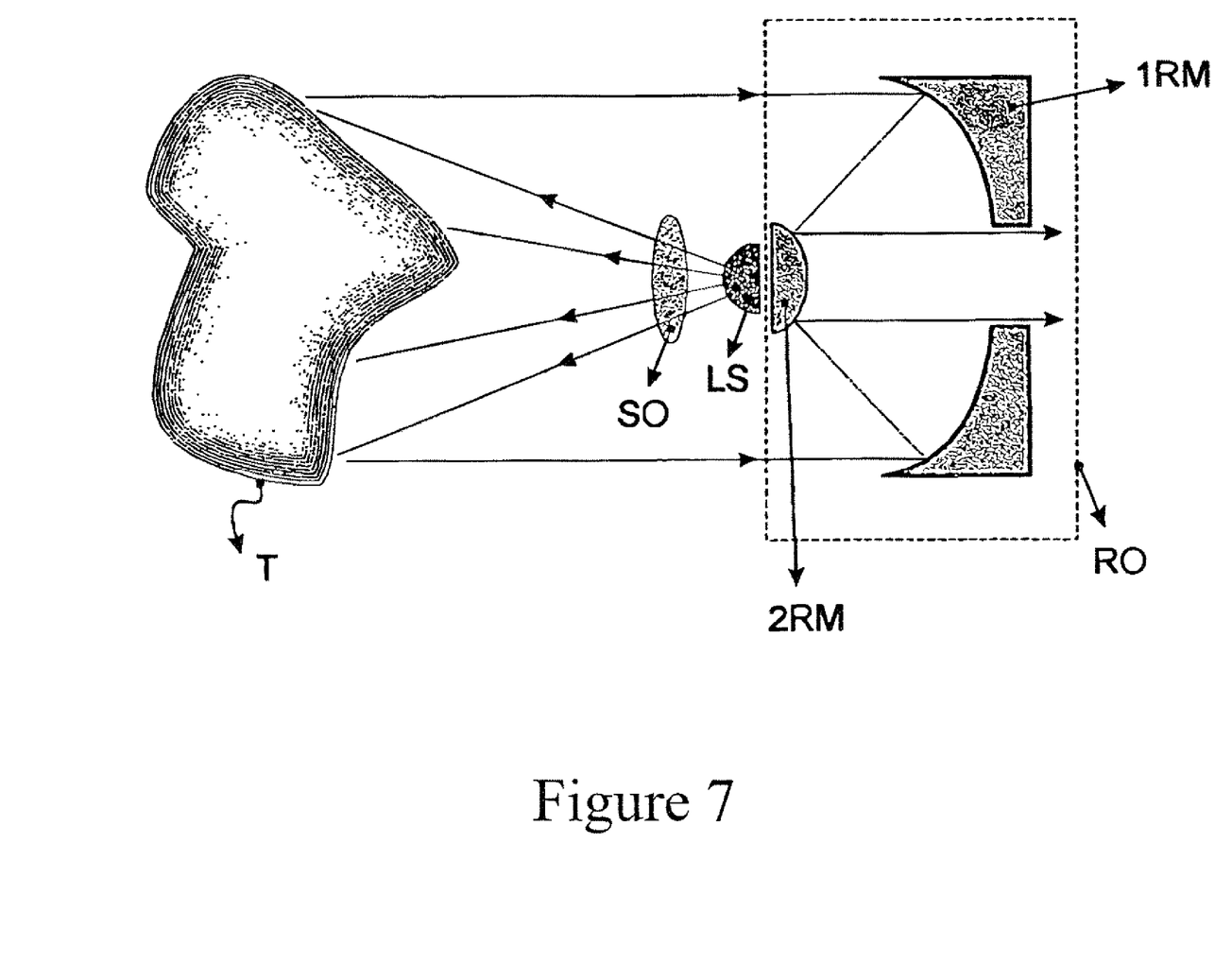
FIG. 7 illustrates an optical imaging apparatus which comprises a light source located at the central part of its frontaperture.

FIG. 7 illustrates an optical imaging apparatus which comprises a light source located at the central part of its front-aperture. With this arrangement, the central ray of the emitted light cone is coaxial, with the central ray of the light beam that enters the imaging apparatus. This enables illumination rays to reach directly the tissue surface under examination and not after multiple reflections in the wall of the cavity. A reflective-objective lens is used, consisted at least of a first reflection (1RM) and a second reflection (2RM) mirror, where at the rear part of the first reflection mirror (2RM), a light source (LS) is attached together (if required) with optics for light beam manipulation such as zooming and focusing (SO). The reflective objective lens (RO), by replacing the common refractive-objective, which is used in conventional microscopes, provides imaging capability in cavities of small diameter, with freedom in choosing the working distance. The zooming and focusing optics of the light beam can be adjusted simultaneously with the mechanism for varying the magnification of the optical imaging system, so that the illumination area and the field-of-view of the imaging system, are varying simultaneously and proportionally. This has as a result, the preservation of image brightness regardless of the magnification level of the lens. The imaging-illumination geometry embodied in this optical imaging apparatus among with the light beam manipulation options, enable the efficient elimination of the contribution of the surface reflection to the captured image and consequently the efficient clinical implementation of the method described herein.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A method for monitoring the effects of a pathology differentiating agent on a sample, the method comprising the steps of:
   (a) exposing the sample to linearly polarized light;
   (b) applying a pathology differentiating agent on the sample;
   (c) initiating a measurement period relative to said applying step, wherein the application of the pathology differentiating agent to the sample and the initiation of the measurement period are synchronized;
   (d) capturing a plurality of successive images of said sample during said measurement period;
   (e) measuring an optical signal observed from said sample within said measurement period;

wherein a relative motion between the sample and an optical head is substantially eliminated in order to substantially align the spatial points of the sample and the optical head.

2. The method of claim 1, wherein said applying step comprises applying said pathology differentiating agent as a mist in a predefined pattern on said tissue.

3. The method of claim 2, wherein said mist is a controlled volume.

4. The method of claim 2, wherein said applying occurs at a controlled rate.

\* \* \* \* \*